United States Patent [19]

Jewett

[11] Patent Number: 4,464,563
[45] Date of Patent: Aug. 7, 1984

[54] INTRAVENOUS FLUID WARMER

[76] Inventor: Warren R. Jewett, 2815 E. Fort Lowell, Tucson, Ariz. 85716

[21] Appl. No.: 297,423

[22] Filed: Aug. 28, 1981

[51] Int. Cl.³ .......................... A61M 5/14; B67D 5/62; F24H 1/12; H05B 1/02

[52] U.S. Cl. ..................................... 219/298; 128/399; 137/341; 165/46; 165/170; 219/299; 219/302; 219/305; 219/308; 219/328; 219/330; 222/146 HE; 604/114

[58] Field of Search ................................ 219/296-299, 219/301-305, 308, 309, 311, 328, 330, 331, 521, 385; 165/169, 154, 170, 46; 128/399, 272, 214 A; 239/135, 136, 133; 222/146 HE; 604/113, 114; 137/341

[56] References Cited

U.S. PATENT DOCUMENTS

| | | | |
|---|---|---|---|
| 1,419,225 | 6/1922 | Colebrook | 219/299 X |
| 1,514,813 | 11/1924 | Adams | 219/305 |
| 1,695,227 | 12/1928 | Bolinger | 219/299 |
| 1,772,557 | 8/1930 | Schumers | 219/299 |
| 1,809,077 | 6/1931 | Shuman | 219/299 |
| 1,960,417 | 5/1934 | Pain, Jr. | |
| 2,470,481 | 5/1949 | Freeman | |
| 2,686,863 | 8/1954 | Chandler | 219/298 X |
| 2,862,120 | 11/1958 | Onsrud | 165/170 X |
| 3,140,716 | 7/1964 | Harrison et al. | 128/399 |
| 3,247,851 | 4/1966 | Seibert | |
| 3,443,060 | 5/1969 | Smith | 219/302 |
| 3,475,590 | 10/1969 | Pins | 219/302 |
| 3,485,245 | 12/1969 | Lahr et al. | 219/302 |
| 3,551,641 | 12/1970 | Truhan | 219/303 |
| 3,590,215 | 6/1971 | Anderson et al. | 219/299 X |
| 3,601,384 | 8/1971 | Durdin | 165/169 X |
| 3,629,552 | 12/1971 | Edging | 219/302 |
| 3,708,110 | 1/1973 | Unger et al. | 128/272 |
| 4,019,020 | 4/1977 | Bilbee | 219/302 |
| 4,167,663 | 9/1979 | Granzow et al. | 219/309 X |
| 4,309,592 | 1/1982 | Le Boeuf | 219/302 X |

*Primary Examiner*—A. Bartis
*Attorney, Agent, or Firm*—J. Michael McClanahan

[57] ABSTRACT

An intravenous fluid warmer includes an electrically heated warmer module receiving a low volume (10 ml.) disposable cartridge through which the fluid being heated flows. The module is configured as two spaced concentric elongated metallic heating elements having attached electric heaters and defining therebetween an elongated plenum adapted to receive the disposable cartridge. The temperature of the heating elements is individually monitored by separate sensors and an electronic temperature control module maintains the inner heating element at a slightly higher temperature (36° C.) than the temperature (34° C.) at which the outer heating element is maintained. The inner heating element is free floating through a limited range to accommodate manufacturing differences is the disposable cartridge. The cartridge, made of polystyrene or polycarbonate plastic, nests in the plenum in contact with the heating elements. The cartridge has a fluid inlet and outlet at one end and internal guide vanes for spreading the fluid throughout the cartridge for thorough heating prior to discharge.

21 Claims, 12 Drawing Figures

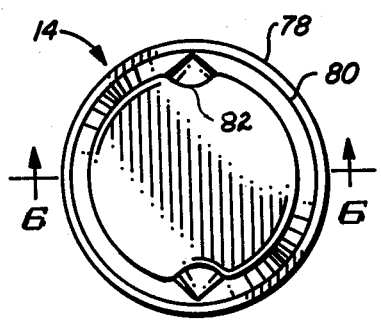
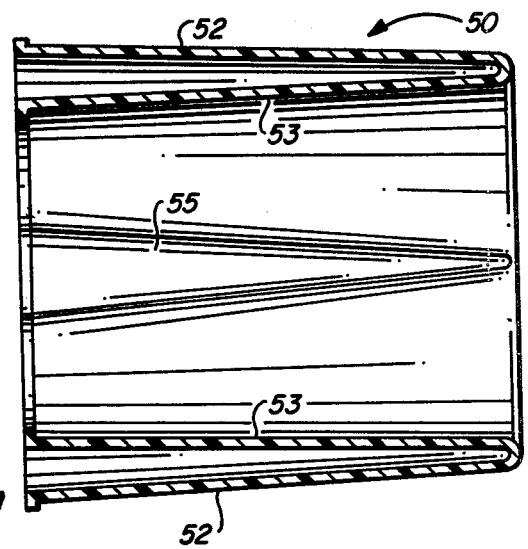
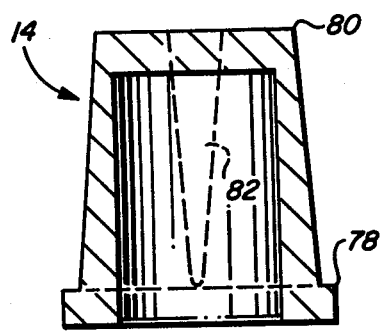
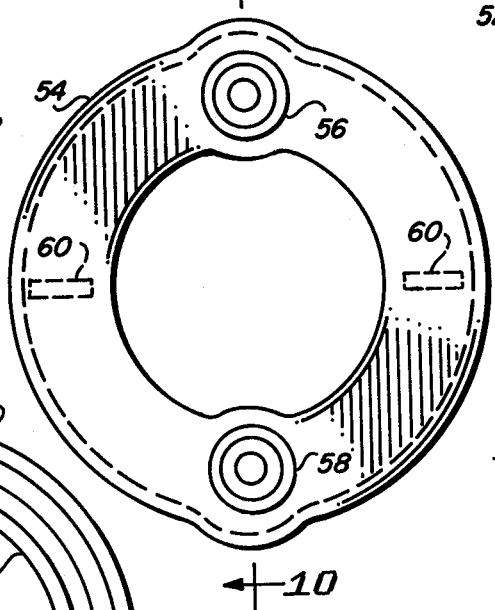
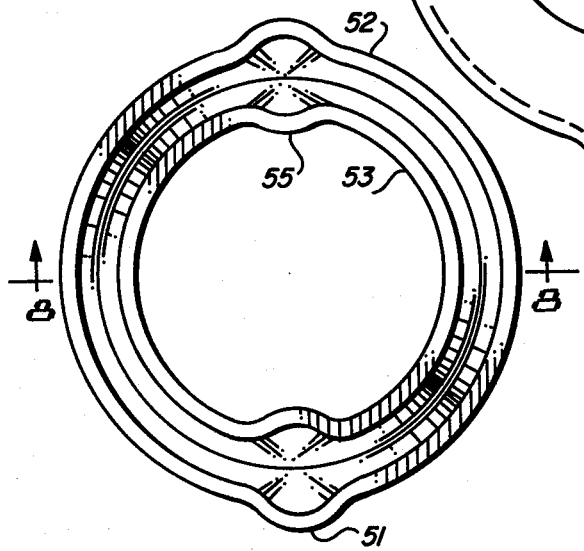
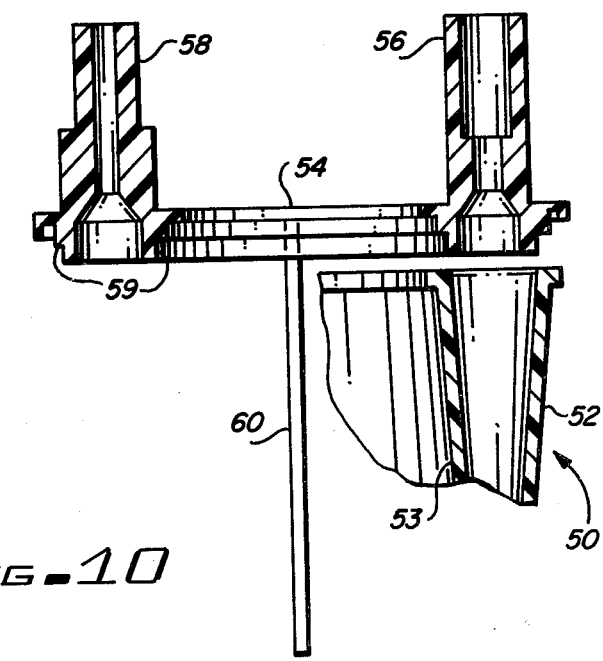

INTRAVENOUS FLUID WARMER

BACKGROUND OF THE INVENTION

Fundamental to the well-being of an infant is the regulation of body temperature. In the new born, an infant weighing less than 5 kg., body temperature is regulated by the metabolism of small brown fat stores. The shiver mechanism, which is an important reflex in the adult, does not become significant until the infant is older.

The loss of body heat and decrease in body temperature can be devastating to an infant. Even with the smallest of temperature losses, in the range of 1½° C., oxygen demand will increae and the shift in metabolic pathways will create a severe metabolic acidosis. Continued decrease in temperature will eventually produce cardiac-respiratory arrest. Fortunately, adults do not usually have these problems.

Common techniques for maintaining temperature include infrared warmers, heating blankets, and warmed intravenous fluids. Adequate means are at hand to provide support for all of these needs with the exception of warming of intravenous (IV) fluids.

No practical fluid warming technique exists for patients weighing less than 10 kg. Devices currently in use have priming volume from between 40 to 70 ml. of fluid and due to their size, must be mounted some distance from the patient. There is therefore a temperature loss at slow intravenous fluid flow rates in the length of tubing interconnecting the warmer and patient. The total fluid weight of these patients is approximately 70% of their weight with circulating fluid volumes of 70 to 80 ml./kg. Thus, a 1 kg. neonate will have an approximate 700 cc total body water and a blood volume of 80 ml. (approximately the priming volume of most fluid warmers). Maintenance fluid requirements for most of these patients is in the range of approximately 4 cc./hr./kg.

The ideal fluid pediatric warmer will have a minimum volume with adequate warming at administration rates of 3 ml./hr. to 100 ml./hr., temperature controlled at 36° C.±1° C.

Prior art fluid warmers are only designed to take the chill off of cooled fluids, and do not achieve body temperatures for the fluid, or in the alternative, do so only for low fluid flow rates.

SUMMARY OF THE INVENTION

The subject invention meets all of the requirements for delivery of intravenous fluids at proper temperature to the previously described patient population as well as having use in adult medicine. It consists of two elements, a disposable plastic cartridge through which the intravenous solution is administered and a metal heating module assembly into which the cartridge is placed. An electronic circuit in the housing of the heater module, responsive to thermal sensors within the heaters, controls electrical power to the heating elements. Temperature is regulated to provide a constant 36° C.±1° C. at the cartridge outlet for fluid flow rates to 100 ml./hr. Higher flows are possible with some temperature degradation. All measurements assume an ambient temperature of 18° C. with fluid temperatures between 4° C. and 18° C.

A feature of the warming technique employed in this invention is the thermal pumping effect. The disposable fluid warming cartridge is a hollow plastic cylinder which nests in a dual heater receptacle. A heating element in contact with the inner wall is set to 36° C. and generates a thermal path through the fluid in the cylinder to a heating element, set at a lower temperature (34° C.) surrounding the outer cartridge wall. If there is low or no flow, the outer heating range is raised to 36° C. via the thermal path. This heat pumping procedure incorporated with the disposable cartridge designed provides an extremely efficient means for raising the temperature of a small fluid volume rapidly.

The heating module comprises an inner and outer heating element configured as two concentric elongated cylinders, the annular elongated plenum formed between the concentric cylinders having a narrowing thickness, the heating elements heated by attached electrical resistance strip heaters, the temperatures of the heating elements individually monitored by sensors such that the inner heating element is kept slightly warmer than the outer heating element. The inner heating element is movable throughout a limited range and is spring-loaded in its axial direction.

The disposable cartridge comprises a hollow cylinder with wedge-shaped converging sides adapted to nest interiorly to and make contact with the inner and outer heating elements for heating the enclosed fluid, the disposable cartridge is closed at both circular ends with an inlet and an outlet at the larger end and a pair of elongated vanes protrude interiorly axially from the larger end substantially the entire length of the annular elongated plenum in order that fluid entering the lower inlet will spread throughout the total disposable cartridge for thorough heating before it exits the upper outlet.

The small size of the apparatus permits placement of the device immediately adjacent to the patient permitting the use of a short IV line to the patient thereby further minimizing heat loss.

Molded of polystyrene or medical grade polycarbonate, the disposable cartridge has a large surface area for rapid warming even at moderate flow rate. Total volume of the disposable cartridge is less than 10 ml. Truncated design terminating at the outlet port facilitates removal of air bubbles when the recipient pathway is filled.

BRIEF DESCRIPTION OF THE DRAWINGS

FIG. 5 is the top view of the inner heating element.

FIG. 6 is a cross-sectional view of the inner heating element taken along sectional line 6—6 of FIG. 5.

FIG. 7 is a top view of the pair of concentric cylinders comprising the disposable cartridge.

FIG. 8 is a cross-sectional view of concentric cylinders comprising the disposable cartridge taken along sectional line 8—8 of FIG. 7.

FIG. 9 is a top view of the annular top piece attached to the concentric cylinders of the disposable cartridge.

FIG. 10 is a cross-sectional view of the annular top piece taken along sectional lines 10—10 shown in FIG. 9.

DETAILED DESCRIPTION OF THE PREFERRED EMBODIMENT

Figure 1:
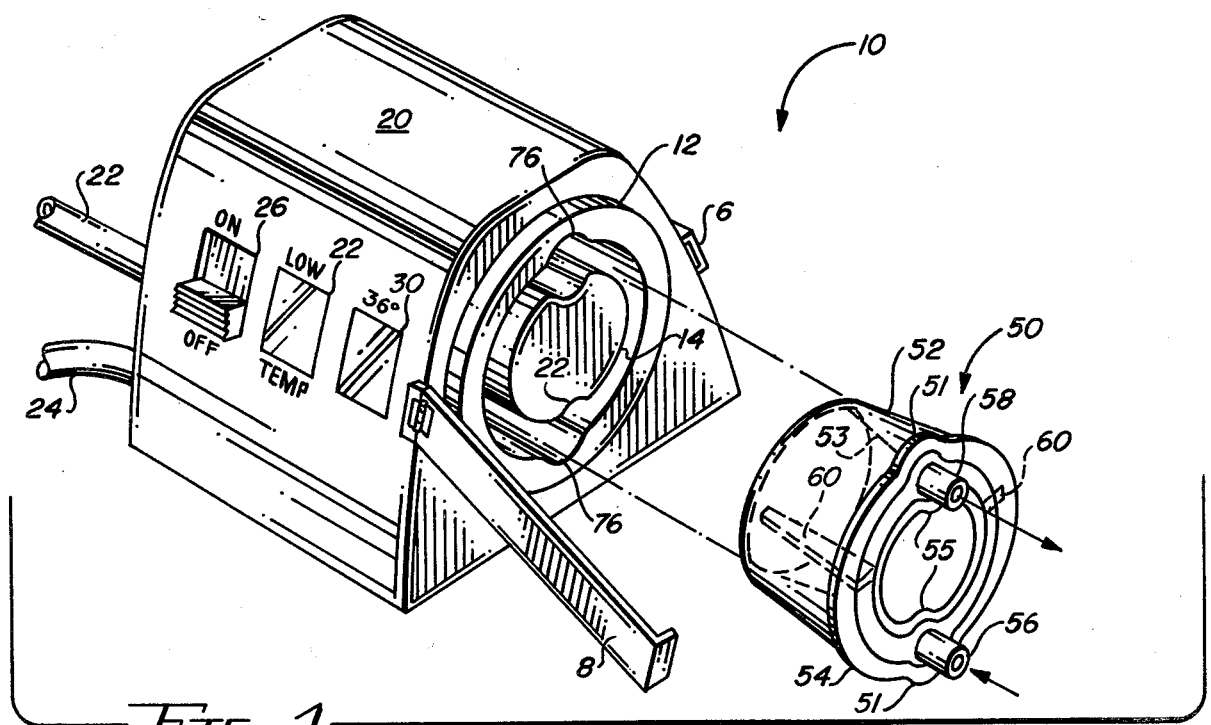
FIG. 1 is a perspective view of the subject inventive warmer module and disposable cartridge.

Referring now to FIG. 1, a perspective view of the subject invention, an apparatus for warming intravenous fluids is shown. Firstly, the invention includes the warmer module 10 to heat the intravenous fluids comprising a permanent type fixture with two concentric cylindrical warming units, namely, an outer heating element 12 and an inner heating element 14. Encompassing the heating elements 12 and 14 is a preferably molded plastic outer case 20 which is attached to an intravenous pole (not shown), a crib (not shown), or an incubator (not shown) by means of accessory clamp 22, a rod-like means attached to case 20 and having a clamp on its distal end (not shown). Electrical power is transmitted to case 20 for heating elements 12 and 14, as well as the electrical lights and switch, by means of electrical cord 24. Shown on one side of case 20 is the electrical power on-off switch 26, the low temperature indicator lamp 28, and the ideal (36° C.) temperature indicator lamp 30.

As shown in FIG. 1, case 20 engages the outside cylindrical wall of outer heating element 12 proximate one end in a securing manner. Inner heating element 14 is disposed centrally to outer heating element 12, inner heating element 14 being attached internally to case 20, as later detailed, with limited side-wise movement and spring-loaded in the axial direction. Formed between outer heater element 12 and inner heater element 14 is an elongated cylindrical plenum having a narrowing or wedge-shaped thickness adapted to receive disposable cartridge 50 in a close fitting thermally conductive configuration. To assure disposable cartridge 50 staying in place and continuing to make a good thermal contact, rigid hinged gate 8 fastened to one side of case 20 is included. On the opposite side, gate 8 connects with latch 6.

Continuing on with the remainder of the invention detailed in FIG. 1, disposable cartridge 50 comprises a polystyrene, polycarbonate, or bio-compatible medical grade plastic formed from two molded components which are ultrasonically bonded. Primarily, the two molded components comprising disposable cartridge 50 are the truncated conical cylindrical volume having one end closed off and formed of rather thin wall high heat conductance plastic or similar type material and a second ring-like annular top piece 54 comprising the same or compatible material. This second component, a flat washer-like piece has an inlet 56 and outlet 58 for entrance and exit of the fluid to be warmed. Attached at right angles to the planar surface of the annular top piece 54 are the elongated vanes 60 (dotted lines). These elongated vanes 60, of which there are at least two, protrude interiorly to the annular plenum formed in the hollow cylinder and serve to direct the fluid to be warmed to the rear of the disposable cartridge 50 in order to compel the fluid flow over the total amount of wall surface between the inlet and the outlet. The elongated vanes 60 protrude on the order of 90% of the distance to the rear of disposable cartridge 50, leaving however an opening between the end of vane 60 and the rear closed off portion of elongated annular plenum formed in part by the outside cylinder wall 52. In addition, there will be a very slight gap between the insides of the elongated annular plenum and the sides of the extended vane 60, however, substantially small enough, given the tolerances of mass production, to allow air to pass between and an extremely small amount of fluid. This assures complete filling of the disposable cartridge 50 by fluid.

Figure 2:
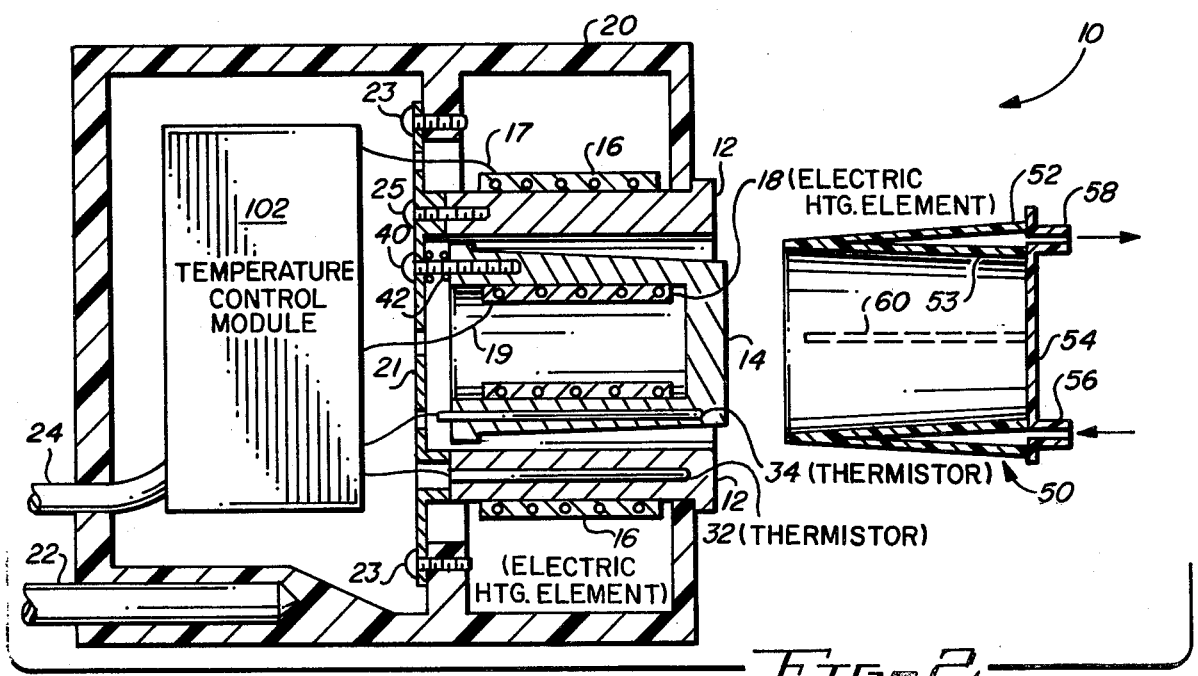
FIG. 2 is a cross-sectional view of the warmer module together with the disposable cartridge.

Referring now to FIG. 2, an elevational cross-sectional view of the warmer module 10 and disposable cartridge 50 is detailed. Beginning with the warmer module 10, exterior case 20 encompasses within its shell the three main components by which the intravenous fluids are heated, namely outer heating element 12, inner heating element 14, and temperature control module 102. As can be seen in FIG. 2, outer heating element 12 defines a cylinder with an inside cylindircal surface forming a conical frustrum (truncated cone) and is fitted with a strip-type band resistance heater 16 wrapped around the outside cylindrical surface. Interiorly to resistance heater 16 are the individual heating resistance wires which actually conduct electricity to generate heat conducted to outer heating element 12. Connecting the strip-type band resistance heater 16 to the temperature control module 102 is electrical lead 17. Inner heating element 14 defines a cylinder with a closed end, the outer surface of which also defines a conical frustrum (truncated cone) having the taper opposite that of outer heating element 12. The means to heat inner heating element 14 is accomplished by a strip-type band resistance heater 18 attached to the inner cylindrical wall, which heater 18 also being electrically connected to temperature control module 102 by means of electrical lead 19. Strip-type resistance heater 18 is connected to the interior cylindrical wall of the inner heater element 14 by means of a heat conducting adhesive.

Outer heating element 12 temperature is monitored by means of thermistor 32 placed in thermal contact with outer heating element 12 by means of a longitudinally drilled hole interiorly to the thickness of the cylindrical wall adapted to receive thermistor 32. The electrical leads connecting the temperature control module 102 with thermistor 32 are shown exiting the rear of thermistor 32. Similarly, the inner heating element 14 has temperature monitoring thermistor 34 inserted into a length-wise drilled hole in the cylindrical wall in order to make thermal contact with the material of the heating element. Thermistor 34 electrical connecting wires, similarily as thermistor 32, run to temperature control module 102.

It is noted that the interior end of outer heating element 12 is firmly attached to case 20 through means of plate 21. Plate 21 is attached at opposite sides by two (or more) threaded screws 23 to an annularly inwardly protruding ring formed in case 20. Outer heating element 12 is fixedly attached to plate 21 by means of at least two threaded screws 25, one of which is shown in FIG. 2.

Inner heating element 14 however, is not fixedly attached to plate 21, but in fact floats in all three axis between imposed limits upon at least two spring-loaded screws 40, one of which is shown in FIG. 2. Screw 40 is screwed into a threaded hole in inner heating element 14 and is thereby fixedly attached to inner heating element 14. However, screw 40 penetrates plate 21 through an oversized hole which allows up, down, and sidewise lateral movement. Then, compression spring 42 is placed between the circular end of inner heating element 14 and plate 21 surrounding the shank of screw 40. Thus, movement of inner heating element 14 is permitted in all directions for reasons that are later discussed. It is noted that the outside circular face of inner heating element 14 extends, in its resting state, slightly beyond the outside flat circular surface of outer heating element 12. This is assured by compression spring 42 urging inner heating element 14 forward. The purpose of this together with the 3-axis freedom of movement is to assure that inner heating element 14 will engage all surfaces of the inner cylindrical surfaces of disposable cartridge 50 in a good thermal conducting manner in order that all parts of the inner cylindrical surface of disposable cartridge 50 receives heat from heating element 14.

Continuing, disposable cartridge 50 is shown in position ready to be inserted into the annular plenum formed between outer and inner heating elements 12 and 14 respectively. Disposable cartridge 50, further defined in the following text, comprises a hollow plastic cylinder formed by two converging elongated cylindrical surfaces to provide a truncated cylindrical volume. The surfaces are so angled as to conform with the tapered cylindrical surfaces of the inner and outer heating elements 12 and 14 in order that when disposable cartridge 50 is placed in the annular plenum formed by heating elements 12 and 14, physical contact is achieved between the metal or other material surfaces of heating element 12 and 14 and the cylindrical surfaces of cylinders 52 and 53. The cylindrical surfaces 52 and 53 are closed at one end, normally done in the molding manufacturing process. The theretofore open end of the cylinders 52 and 53 are closed by means of annular top piece 54 which is ultrasonically bonded to cylinders 52 and 53, and which has attached fluid inlet 56 and outlet 58.

When disposable cartridge 50 is inserted into the plenum formed between outer heating element 12 and inner heating element 14, the annular top piece 54 will engage the circular face of inner heating element 14 and push it backwards until cylindrical surface 52 of disposable cartridge 50 fully engages the inside surface of outer heating element 12. Then disposable cartridge 50 is held in place by friction, compression spring 42 not being strong enough to disengage cartridge 50. In addition, gate 8 (not shown, but shown in FIG. 1) runs across the top piece 54 from side to side connecting to case 20 helping to secure disposable cartridge 50 in place. In this manner, both the inside heating element 14 and the outside outer heating element 12, contact in a good thermal conducting manner the total cylindrical surface of disposable cartridge 50 in order to thermally pump heat from the higher temperature inner heating element 14 into the fluid to be warmed, as well as from the slightly lower temperature outer heating element 12.

To the rear of warmer module 10 shown in FIG. 2 is temperature control module 102 connecting to heaters 16 and 18, thermistors 32 and 34, and to the source of electrical power through power cord 24, power cord 24 also shown in a hole located passing through the wall of the case 20.

Figure 3:
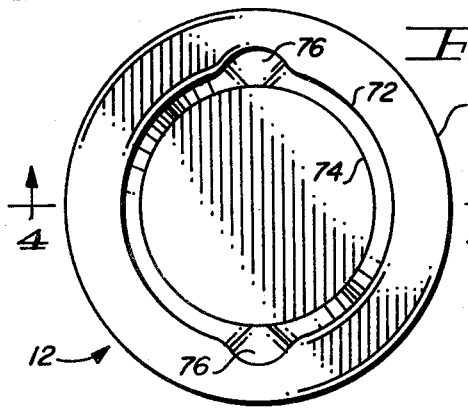
FIG. 3 is a top view of the outer heating element.

Referring now to FIG. 3, a top view of outer heating element 12 is shown. Looking down, the outside peripheral edge if shown as the largest diameter circle, followed inwardly by the circle 72 making up the top peripheral edge of the inner cylindrical wall. Following circle 72 is circle 74 representing the bottom of the interior cylindrical wall of outer heating element 12. Noted at the top and the bottom connecting top peripheral edge 72 are rounded furrows 76 which is an additional arcuate cut made into the interior wall of the cylinder forming outer heating element 12, the arcuate cut taken in the cylinder wall greatest at the top and least at the bottom, the cut blended from top to bottom, the lines formed by the cut into the cylinder wall thereby having a converging taper until they meet at the bottom of cylindrical wall forming circle 74. This rounded furrow 76 cut into the cylindrical wall conforms to a trough 51 formed in the outward cylindrical surface of the disposable cartridge 50 which is shown in a later figure.

Figure 4:
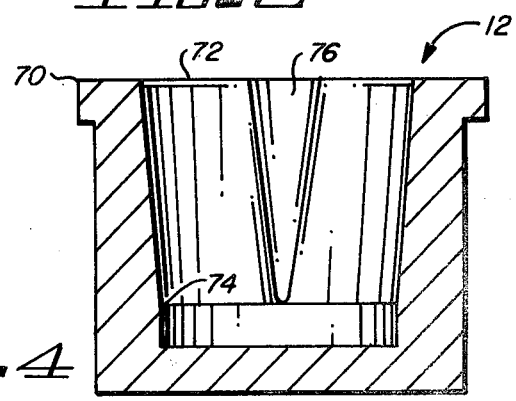
FIG. 4 is an elevational cross-sectional view of the outer heating element taken along sectional lines 4—4 of FIG. 3.

FIG. 4 shows a cross-sectional view of outer heating element 12 taken equi-distant from the rounded furrow 76 at sectional line 4—4 of FIG. 3 in order to show the furrow 76 in full view. Shown in FIG. 4 are the peripheral edges of the outer heating element 12 discussed in FIG. 3 together with the furrow 76 consisting of the arcuate cut made in the interior cylindrical wall of the outer heating element 12 which is blended along the depth of the interior cylindrical wall until it reaches the point of the end of narrowing taper of the interior cylindrical wall.

Referring now to FIG. 5, a top view of the inner heating element 14 is disclosed showing firstly, the outer greatest circle 78 representing the bottom circular edge of the heating element 14, and inner circle 80 representing the top peripheral edge of the same. Formed into the top peripheral edge is furrow 82 which arches inwardly to the inner heating element 14.

Referring to FIG. 6, a side elevational view taken along sectional line 6—6 of FIG. 5 of the inner heating element 14 is detailed showing the top circular peripheral edge 80, the bottom circular edge 78 at the base of the inner heating element 14, and in dotted form the furrow 82 cut longitudinally into the cylindrical side of the heating element. The furrow 82 cut, which is made longitudinally along the outward cylinder side, is blended from the base of the cylinder upward with the maximum cut taken at the top. Additionally shown in FIG. 6 is the cylindrical interior wall of the inner heating element 14.

Referring now to FIG. 7, a top view of disposable cartridge 50 concentric cylinders 52 and 53 is detailed. As indicated earlier, the concentric cylinders which form the portion of disposable cartridge 50 in which the fluid flows and which are in thermal contact with the outer and inner heating elements are two converging cylinders which are joined at the bottom. The inner cylinder 53 is an upwardly directed conical frustum, and the outer cylinder 52 is a downwardly directed conical frustum. Along the cylindrical sides of both cylinders 52 and 53, the plastic material is arched to form longitudinal troughs 51 and 55 in outer and inner cylinders 52 and 53 respectively. These troughs 51 and 55 are complimentary to furrows 76 and 82 of the outer and inner heating elements 12 and 14 respectively.

Referring now to FIG. 8, an elevational sectional view of cylinders 52 and 53 comprising disposable cartridge 50 is shown taken through the sectional line 8—8 of FIG. 7. The cylinders 52 and 53 show opposite going conical frustums or, if you will, truncated cones, detailing the narrowing annular plenum formed between, and their closure with each other at the bottom. Centrally to FIG. 8 is the outline of trough 55 of inner cylinder 53, showing trough 55 to be greatest at the top and then blending downward to a point at the bottom where the two cylinders are joined. Trough 51 repeats the same narrowing from the top to the bottom as does trough 55, but only on a slightly larger scale, since it is part of a slightly larger cylinder 52.

Referring now to FIG. 9, a top view of the annular top piece 54 of disposable cartridge 50 is detailed. Firstly, annular top piece 54 is formed of the same plastic or other similar compatible material which comprises concentric cylinders 52 and 53. The annular top piece is designed to cover the annularly shaped top opening between concentric cylinders 52 and 53 and to be ultrasonically bonded or welded to the top peripheral rims of concentric cylinders 52 and 53. Shown on opposite sides of annular top piece are the inlet and outlet 56 and 58 respectively. It is noted that in the area of the inlet and outlet the annular top piece edges have been expanded to accomodate the inlet and outlet fixtures as well as to conform to troughs 51 and 55 of cylinders 52 and 53. The central section of annular top piece 54 is open as shown in FIG. 9. Equal distance from the inlet and outlet, and centrally located on the annular top piece 54 are elongated vanes 60, shown here in dotted form. These vanes protrude into the annular plenum formed by the two concentric cylinders 52 and 53 in order to direct the flow of the fluid to be warmed toward the rear part of the disposable cartridge 50 in order to assure the fluid coming into the plenum lower inlet flows throughout the plenum and thereby is in contact with all surface of the heating elements, both inner and outer, and does not merely travel from the lower inlet to the upper outlet of the disposable cartridge 50.

FIG. 10 is a cross-sectional view of annular top piece 54 taken along sectional line 10—10 shown in FIG. 9. In FIG. 10, the inlet and outlet fixtures 56 and 58 predominate showing their attachment to annular top piece 54 and are nominally one piece. Additionally shown is elongated vanes 60 attached to top piece 54. These vanes 60, of which there are at least two, protrude, when assembled, nearly to the bottom joinder of the cylinders 52 and 53 and are so designed to be tapered and thus conform to the interior narrowing space between concentric cylinders 52 and 53. Shown also in FIG. 10 are the additional plastic material termed "force directors" 59 which comprise additional material in the shape of an annular shoulder formed as part of the annular top piece 54 which presents an obstacle to the insertion of inside peripheral top edge of the two concentric cylinders 52 and 53. At the time that the concentric cylinders 52 and 53 are bonded to annular top piece 54 by ultrasonic heating, these force directors, which run totally around the annular top piece 54, will melt and flow allowing the concentric cylinders top rims to move upward into an annular groove opened by the flowing force directors. The material of the force directors then seal the annular plenum formed by the two concentric cylinders 52 and 53 to the annular top piece. It is anticipated that the annular top piece 54 will be made by plastic molding in one single piece.

For ease of illustration, a partial section of concentric cylinders 52 and 53 are shown in place in FIG. 10 ready to be urged against the annular top piece 54 showing the relationship of the force directors 59 for melting and sealing the annular top piece 54 to concentric cylinders 52 and 53.

Figure 11:
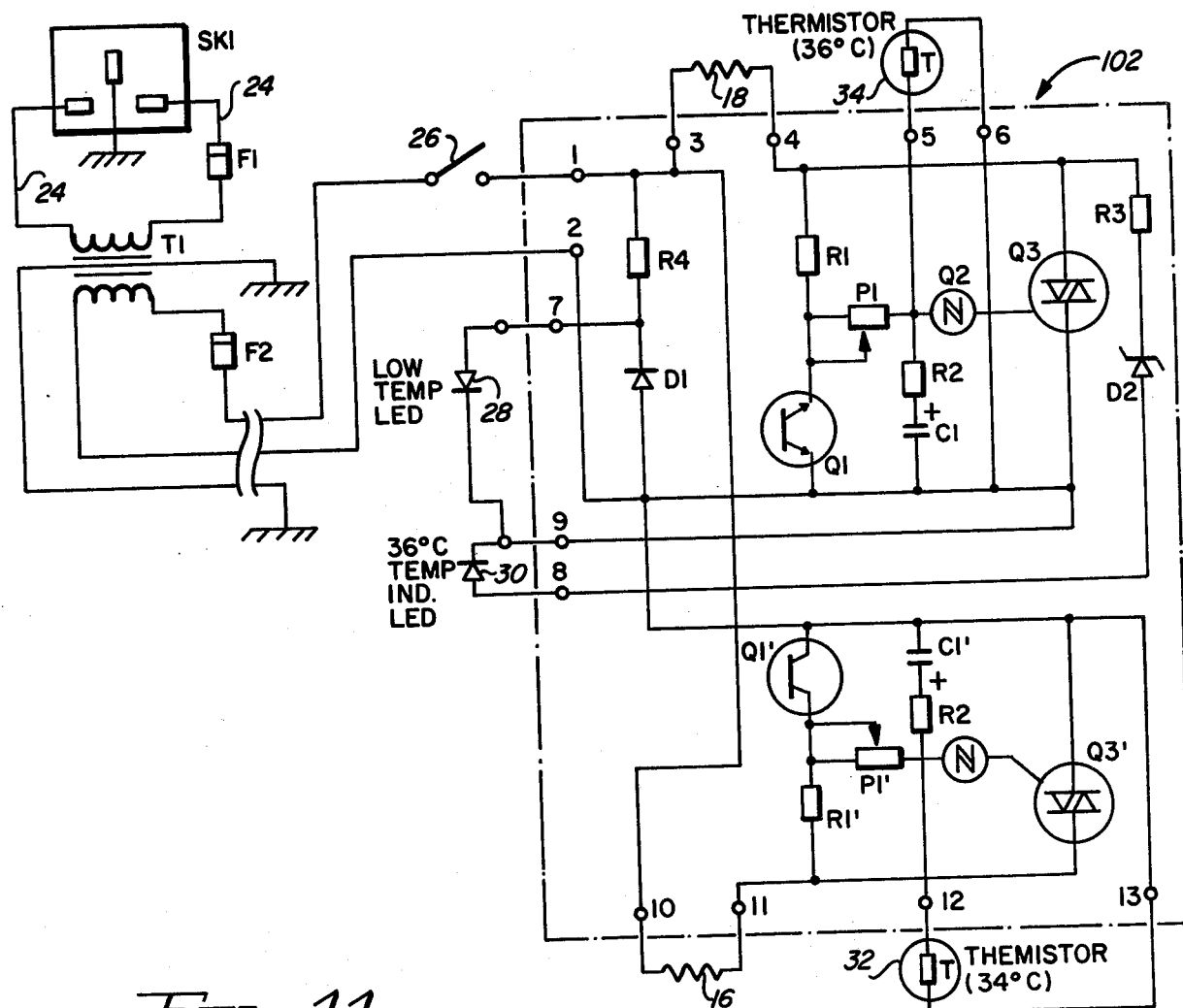
FIG. 11 is the electrical schematic of the temperature control module regulating temperature of the inner and outer heating elements.

Referring now to FIG. 11, an electrical schematic of the temperature control module 102 is detailed. Starting at the top of FIG. 11, first shown is SK1, the electrical plug for insertion into a wall receptacle to obtain a source of either 120 or 220 volt AC power. One side of the 120 volt AC is fused through fuse F1 and then transformed to a lower voltage, nominally 12 volts AC, by means of step-down transformer T1. Here again, one side of the 12 volt AC is fused by means of fuse F2 whereupon the electrical current is transmitted to the temperature control module 102 through a six foot or two meter extension cord. Ground is carried all the way through as seen in FIG. 11. The 12 volt AC electrical power entrance is interrupted by means of on-off switch 26 (FIG. 1) prior to its entrance into temperature control module 102. Upon the entrance of electrical power into temperature control module 102, the presence of same is sensed through resistor R4 and diode D1 which in turn gives indication through light emitting diode 28 which, upon the immediate entrance of electrical power, is illuminated. This light is the low temperature light 28 on the warmer module 10 as shown in FIG. 1. Thereafter, electrical power is directed to electrical resistance 18 of the inner heating element 14 (shown in FIG. 2 as inner heater element 14 strip-type band resistance heater 18). Electrical current through resistor heater 18 is controlled by thermistor 34 (which corresponds to thermistor 34 shown in FIG. 2). When thermistor 34 resistance indicates that 36° has been reached by the inner heating element 14 due to heat generated by electrical resistance 18, the light emitting diode 30 (36° C. temperature indicator on FIG. 1) is illuminated and electrical current through resistance 18 is terminated. Thereafter, current through resistance 18 is regulated by sensor (thermistor) 34. Temperature is maintained at 36° C.±1° C. on the inner cylindrical heating element 14.

The electrical circuit operating the electrical resistance 16 for outer cylindrical heating element 12 by sensing sensor (thermistor) 32 is shown below the circuit for the inner cylindrical heating element 14 in FIG. 11. By adjustment of potentiometer P1', temperature of the outer heating element 12 is maintained at 34° C.±1° C. The two circuits are identical except the additional elements added for take-off of the light emitting diodes 28 and 30.

The electrical circuit shown in FIG. 11 is within the state of the art, it being an adaption for 12 volt AC from a circuit shown in General Electric SCR Manual, 5th Edition, 1972, pages 330–331. Reference is made to such manual.

Figure 12:
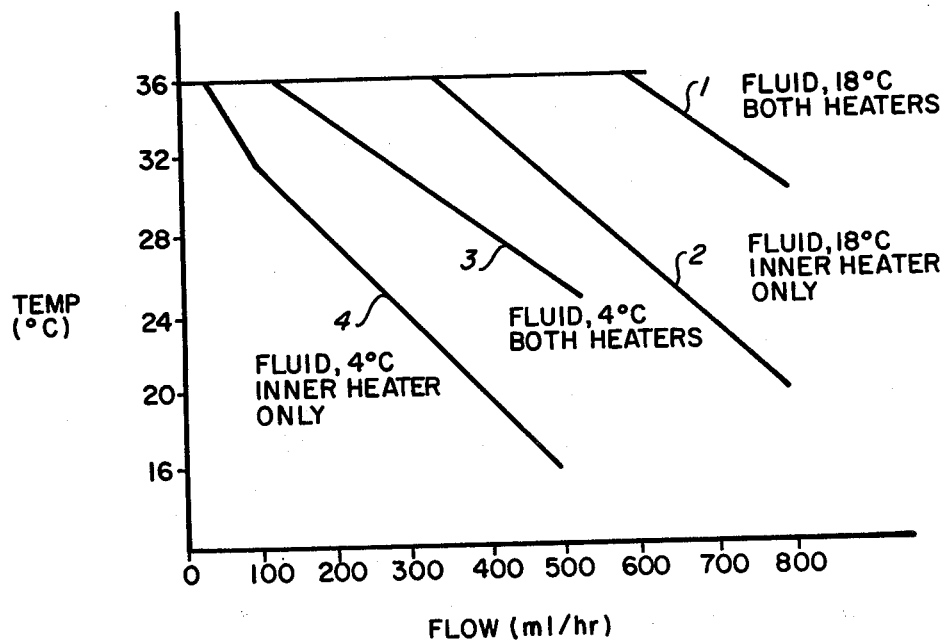
FIG. 12 is a graph showing intravenous fluid outlet temperature vs. fluid flow rate.

Referring now to FIG. 12, a computer generated graph showing the effect of thermal pumping of the heat from the inner cylindrical heater to the outer cylindrical heater upon fluid temperature is shown. In all plots, the environment (surrounding air) was at a temperature of 18° C. Plot 1 (solid line) shows temperature v. fluid flow for the inner and outer heaters maintained at their respective temperatures with the intravenous fluid solution at ambient temperature (18° C.). Plot 2 (short dotted line) shows the intravenous fluid at ambient temperature (18° C.), but only an inner heater is utilized and the outside of the disposable cartridge is open to the environment. Plot 3 (longer dotted line) shows the temperature v. fluid flow for the inner and outer cylindrical heaters maintained at their temperature and the intravenous solution initially chilled to 4° C. Finally, Plot 4 (center-line type line) shows the temperature v. fluid flow utilizing only an inner heater with the outside of the disposable cartridge open to ambient environment and the fluid initial temperature chilled to 4° C. The effect of thermal pumping of the heat from the inner heater to the outer heater is much apparent from FIG. 12.

In operation, the invention works by the nurse or operator first filling the disposable cartridge with the fluid which is to be intravenously fed to the patient. It is anticipated that the plastic used in the disposable cartridge shall be transparent, or translucent, and the fluid progress through the annular plenum can be observed. The disposable cartridge may be shaken in order to assure that all of the air inside is first bled from the outlet so that when the cartridge is inserted into the warmer module it has been completely primed with fluid. As indicated earlier, priming will take less than 10 ml. of intravenous fluid. The cartridge then is inserted into the warmer module being keyed by means of the troughs on the sides of the disposable cartridge and the corresponding furrows on the heating elements of the warmer module. The nurse has to, however, ascertain that the inlet is at the lower level.

The disposable cartridge is pushed into the warmer module until the outside of the disposable cartridge surface makes full contact with the outer heating element. At that time, full contact with the inner heating element will have already been made, since it will be pushed backwards by insertion of the disposable cartridge and since the inner heating element is free floating, it is free to adjust to full contact with the disposable cartridge and can therefore conform to any manufacturing differences in the disposable cartridge. The hinged gate on the front of the heater module is then latched in place.

Because of the method by which the outer and inner heating elements are heated, and the temperature difference across them, the disposable cartridge and the fluid thereinside will be thermally pumped with heat and thus assure very rapid transfer of heat into the fluid. The hotter inner heater attempts to bring the fluid and the outer heater to the temperature of the inner heater so there is the effect of thermally pumping heat across the fluid and thereby heating the fluid.

Upon completion of the intravenous injection, the disposable cartridge is removed and discarded. The warmer module is a permanent fixture which may be left on or off, as the operator desires and since it is temperature regulated, will not overheat if left on with or without the disposable cartridge inserted.

While a preferred embodiment of the device has been shown and described, it will be understood that there is no intent to limit the invention by such disclosure, but rather it is intended to cover all modifications and alternate constructions falling within the spirit and the scope of the invention as defined in the appended claims.

I claim:

1. A warmer module for warming a fluid comprising an elongated cylindrical outer heater and a concentrically located elongated cylindrical inner heater within said outer heater, said outer and inner heater so shaped as to define an elongated annular cylindrical tapering plenum therebetween adapted to receive an associated cartridge in the annular plenum, and further comprising means for mounting said inner elongated cylindrical heater within said outer heater while permitting limited freedom of movement of said inner cylindrical heater within said outer cylindrical heater to accommodate the associated cartridge.

2. The warmer module as defined in claim 1 wherein said means for mounting said inner elongated cylindrical heater within said outer elongated cylindrical heater includes means spring loading said inner elongated cylindrical heater in the axial direction of said outer elongated cylindrical heater.

3. The warmer modile as defined in claim 2 wherein said means for mounting said inner heater while permitting limited movement of said inner heater within said outer heater defines a plate fixedly connected to said outer heater, a pin fixedly connected to said inner elongated cylindrical heater and extending freely through an opening in said plate, a compression spring surrounding a portion of said pin, said compression spring interposed said inner elongated cylindrical heater and said plate and means limiting relative movement between said plate and said inner heater.

4. The warmer module as defined in claim 3 wherein said fluid to be warmed comprises an intravenous fluid for injection into a patient.

5. The warmer module as defined in claim 1 wherein said fluid to be warmed comprises an intravenous fluid for injection into a patient.

6. A warmer module for warming a fluid comprising an elongated cylindrical outer heater, a concentrically located elongated cylindrical inner heater within said outer heater, and a temperature control assembly, said outer and inner heaters being so shaped as to define an elongated annular cylindrical tapering plenum therebetween, each of said outer and inner heaters including respectively, electrical heating elements attached thereto, and further including a separate temperature sensor attached to each of the outer elongated cylindrical heater and the inner elongated cylindrical heater; said temperature control assembly electrically connected to each of said inner and outer elongated cylindrical heater electrical heating element, and to each of the inner and outer elongated cylindrical heater temperature sensor, said temperature control assembly adapted to separately control the temperatures, respectively, of the inner and outer elongated cylindrical heaters simultaneously at two different temperatures in response to the temperature sensed by the sensor associated with each respective cylindrical heater.

7. The warmer module as defined in claim 21 wherein said temperature control assembly, simultaneously maintains the inner elongated cylindrical heater temperature at a temperature of 36° C., and maintains the outer elongated cylindrical heater temperature at 34° C.

8. The warmer module as defined in claim 7 wherein said fluid to be warmed comprises an intravenous fluid for injection into a patient.

9. The warmer module as defined in claim 6 wherein said fluid to be warmed comprises an intravenous fluid for injection into a patient.

10. A disposable cartridge adapted to receive for warming a fluid comprising a cartridge adapted to be placed in heat conductance relationship with a source of heat, said cartridge also adapted to receive the fluid from a source, to permit conveyance of heat to the fluid, and to release the warmed fluid, said cartridge defining a hollow closed annular cylinder having two ends, an outside elongated cylindrical wall, and an inside concentric cylindrical wall, said walls joined to form a first end of the annular cylinder; and a flat annular ring joining both said outside and said inside cylindrical walls to form the second end of the annular cylinder, said flat annular ring having a fluid inlet and a fluid outlet therethrough communicating with the interior of said hollow closed cylinder, and further comprising at least two elongated vanes situated interiorly to said hollow closed annular cylinder, said elongated vanes attached at one end to said flat annular ring and extending axially into said hollow closed annular cylinder for directing the fluid from the inlet to the first end of the annular cylinder prior to discharge of the fluid from the outlet.

11. The cartridge for warming fluid as defined in claim 10 wherein said fluid inlet and said fluid outlet are located opposite each other on said flat annular ring, and said elongated vanes situated in said hollow closed annular cylinder are opposite each other and mid-way between said fluid inlet and said fluid outlet.

12. The cartridge for warming fluid as defined in claim 11 wherein said cartridge outside cylindrical wall and inside concentric cylindrical wall each define tapering walls, both said tapering walls adapted to be engaged by the source of heat whereupon the fluid interiorly to said cartridge may be placed in thermal contact with the source of heat and thereby be warmed.

13. The disposable cartridge for warming fluid as defined in claim 12 wherein said fluid to be warmed comprises an intravenous fluid for injection into a patient.

14. The disposable cartridge for warming fluid as defined in claim 10 wherein said fluid to be warmed comprises an intravenous fluid for injection into a patient.

15. In combination, a warmer modile for warming a fluid and a disposable cartridge to contain fluids while being warmed, the combination comprising an elongated cylindrical outer heater and a concentrically located elongated cylindrical inner heater within said outer heater, said outer and inner heater so shaped as to define an elongated annular cylindrical plenum having tapering cylindrical walls, and a removable cartridge adapted to be engaged by said inner and outer heaters and to occupy the elongated annular cylindrical plenum, said cartridge defining an annular cylinder having elongated tapering cylindrical walls complimentary to said elongated tapering cylindrical walls of said outer and inner cylindrical heaters, and a fluid inlet and a fluid outlet, and said warmer module further comprising means for mounting said inner elongated cylindrical heater in said outer heater while permitting limited freedom of movement of said inner heater within said outer heater.

16. The combination as defined in claim 15 wherein said means for mounting said inner elongated heater in said outer elongated cylindrical heater provides spring loading in the axial direction of said inner heater relative to said outer elongated cylindrical heater to allow limited freedom of movement of said inner heater within said outer heater to accomodate said cartridge.

17. The combination as defined in claim 16 wherein said inner and outer elongated cylindrical heaters include respective heating elements attached to each heater, and a separate temperature sensor attached to each of the inner and outer elongated cylindrical heaters whereby the temperature of each of the cylindrical heaters may be separately sensed.

18. The combination as defined in claim 17 further including a temperature control assembly, said temperature control assembly electrically connected to each of said inner and outer elongated cylindrical heater electrical heating element and to each of the inner and outer elongated cylindrical heater temperature sensor, said temperature control assembly responsive to said temperature sensors and simultaneously maintaining the temperatures, respectively, of the inner and outer elongated cylindrical heaters at different levels.

19. The combination as defined in claim 18 wherein said temperature control assembly controls heating and maintains the inner elongated cylindrical heater temperature at a temperature of 36° C., and simultaneously maintains the outer elongated cylindrical heater temperature at a temperature of 34° C.

20. The combination as defined in claim 19 wherein said fluid warmed in said warmer module and contained in said disposable cartridged comprises intravenous fluid for injection into a patient.

21. The combination as defined in claim 15 wherein said fluid warmed in said warmer module and contained in said disposable cartridges comprises intravenous fluid for injection into a patient.

* * * * *

UNITED STATES PATENT AND TRADEMARK OFFICE
CERTIFICATE OF CORRECTION

PATENT NO. : 4,464,563

DATED : August 7, 1984

INVENTOR(S) : Warren R. Jewett

It is certified that error appears in the above-identified patent and that said Letters Patent is hereby corrected as shown below:

Claim 7, line 1, delete "21", and insert -- 6 --.

Claim 7, line 2, delete ",".

Signed and Sealed this

Twenty-sixth Day of February 1985

[SEAL]

Attest:

DONALD J. QUIGG

Attesting Officer

Acting Commissioner of Patents and Trademarks